United States Patent
Kodani et al.

(10) Patent No.: US 10,084,292 B2
(45) Date of Patent: Sep. 25, 2018

(54) METHOD AND APPARATUS FOR PRODUCING A POLARIZED RESIN FILM

(71) Applicants: DAIKIN INDUSTRIES, LTD., Osaka (JP); TOHO KASEI CO., LTD., Nara (JP)

(72) Inventors: Tetsuhiro Kodani, Osaka (JP); Eri Mukai, Osaka (JP); Takashi Kanemura, Osaka (JP); Meiten Kou, Osaka (JP); Susumu Kawato, Nara (JP); Satoshi Shimizu, Nara (JP)

(73) Assignees: DAIKIN INDUSTRIES, LTD., Osaka (JP); TOHO KASEI CO., LTD., Nara (JP)

( * ) Notice: Subject to any disclaimer, the term of this patent is extended or adjusted under 35 U.S.C. 154(b) by 0 days.

(21) Appl. No.: 15/827,087

(22) Filed: Nov. 30, 2017

(65) Prior Publication Data

US 2018/0097338 A1     Apr. 5, 2018

Related U.S. Application Data

(62) Division of application No. 14/655,988, filed as application No. PCT/JP2013/085216 on Dec. 27, 2013, now Pat. No. 9,865,996.

(30) Foreign Application Priority Data

Dec. 28, 2012  (JP) .................................. 2012-288103
Sep. 6, 2013   (JP) .................................. 2013-185470

(51) Int. Cl.
   *G01N 21/00*      (2006.01)
   *H01T 19/04*      (2006.01)
   (Continued)

(52) U.S. Cl.
   CPC .............. *H01T 19/04* (2013.01); *C08J 7/123* (2013.01); *G01N 21/8422* (2013.01);
   (Continued)

(58) Field of Classification Search
   CPC ....... H01T 19/04; C08J 7/123; C08J 2327/16; G01N 21/8422; G01N 21/896; G01N 2021/8965
   See application file for complete search history.

(56) References Cited

U.S. PATENT DOCUMENTS 6,259,960 B1 *  7/2001  Inokuchi ............ G01N 21/9501
                                                    250/310
2007/0285655 A1  12/2007  Shimoda
2007/0285665 A1 * 12/2007  Shimoda ................. G01N 21/21
                                                    356/430

FOREIGN PATENT DOCUMENTS

JP        7-137114       5/1995
JP        2002-226615    8/2002
(Continued)

OTHER PUBLICATIONS

International Search Report dated Mar. 11, 2014 in International (PCT) Application No. PCT/JP2013/085216.

*Primary Examiner* — Jamil Ahmed
(74) *Attorney, Agent, or Firm* — Wenderoth, Lind & Ponack, L.L.P.

(57) ABSTRACT

An object of the present invention is to provide a polarized vinylidene fluoride/tetrafluoroethylene copolymer resin film that can significantly reduce, when used as an optical film, the deterioration of the quality of video or still images formed by display elements.
The present invention provides a polarized vinylidene fluoride/tetrafluoroethylene copolymer resin film having 2,000 or fewer spot defects per $m^2$, the number of spot defects being measured by a defect measurement method;
the method using an surface inspection system in which a CCD camera is placed so as to detect defects at an angle of 45 degrees relative to an LED source, defects of the film are read within a rectangular range of 300 mm in a width direction (the direction perpendicular to the scanning direction), and 150 mm in a machine direction (Continued)

(the scanning direction), while the film is scanned under the camera at a rate of 20 m/min;

wherein first, defects having a bright area of 1.5 mm$^2$ or less and a dark area of 1.4 mm$^2$ or less are selected; and next, in order to remove defects resulting from causes other than a corona treatment contained in these defects, a circumscribed rectangle of defect is set so as to have two sides along the scanning direction, and the number of only defects that have a circumscribed width of 2.88 mm or less, a circumscribed length of 2.3 mm or less, an aspect ratio of −39 to +27, an occupancy area ratio in the circumscribing rectangle of 4,000 to 6,950, and an area ratio of −3,100 to +5,200, is automatically counted as spot defects by the surface inspection system.

14 Claims, 2 Drawing Sheets

(51) Int. Cl.
G01N 21/84 (2006.01)
C08J 7/12 (2006.01)
G01N 21/896 (2006.01)

(52) U.S. Cl.
CPC ........ *G01N 21/896* (2013.01); *C08J 2327/16* (2013.01); *G01N 2021/8965* (2013.01)

(56) References Cited

FOREIGN PATENT DOCUMENTS

| | | | | |
|---|---|---|---|---|
| JP | 2002226615 A | * | 8/2002 | ............. B29C 47/08 |
| JP | 2003-326542 | | 11/2003 | |
| JP | 2004-149571 | | 5/2004 | |
| JP | 2004-330651 | | 11/2004 | |
| JP | 2005-138562 | | 6/2005 | |
| JP | 2006-47532 | | 2/2006 | |
| JP | 2006-142774 | | 6/2006 | |
| JP | 2006-154709 | | 6/2006 | |
| JP | 2008-101166 | | 5/2008 | |
| JP | 2010-26938 | | 2/2010 | |
| JP | 2010-76128 | | 4/2010 | |
| JP | 2010-100746 | | 5/2010 | |
| JP | 2011-181748 | | 9/2011 | |
| JP | 2011181748 A | * | 9/2011 | ................ C08J 7/00 |
| JP | 2012-118479 | | 6/2012 | |

* cited by examiner

METHOD AND APPARATUS FOR PRODUCING A POLARIZED RESIN FILM

TECHNICAL FIELD

The present invention relates to a polarized resin film and a method for producing the same.

BACKGROUND ART

Display and input devices provided with a display device (e.g., a liquid crystal display) and a touch panel, which is an input device, placed in front of the display device have been put to practical use, and have been used in the operation panels of portable devices (e.g., mobile phones) and electrical home appliances. Display and input devices using touch panels enable users to intuitively operate the instrument by pressing the display on the screen.

In such a display and input device using a touch panel, the touch panel is placed in front of the display device, and is therefore required to have high transparency so as to increase the visibility of the display of the display device.

Mobile phones and tablet computers equipped with touch panels have rapidly spread in recent years. Their displays are viewed from a close distance, and are thus required to have a very high image quality.

Various resin films are used as optical films in such displays, and the quality of the resin films can have a large impact on the image quality of the displays.

Factors adversely affecting the quality of the optical films include, for example, the uneven thickness of the film, deposits of additives in the resin composition, unmelted parts of the resin, scratches, crosslinked gels formed from the resin, etc. Techniques for solving each of these factors are proposed (for example, PTL 1 to PTL 11).

Meanwhile, highly transparent touch panels that can detect the height (strength) of pressing force are proposed. As such a touch panel, for example, PTL 12 proposes a touch panel comprises a transparent piezoelectric layer containing a vinylidene fluoride/tetrafluoroethylene copolymer that has a low total haze value.

Further, PTL 13 discloses a polarized vinylidene fluoride/tetrafluoroethylene copolymer film that has substantially no anisotropy and has few scratches on the surface.

CITATION LIST

Patent Literature

PTL 1: JP2003-326542A
PTL 2: JP2004-149571A
PTL 3: JP2004-330651A
PTL 4: JP2005-138562A
PTL 5: JP2006-47532A
PTL 6: JP2006-142774A
PTL 7: JP2006-154709A
PTL 8: JP2008-101166A
PTL 9: JP2010-76128A
PTL 10: JP2010-100746A
PTL 11: JP2012-118479A
PTL 12: JP2010-026938A
PTL 13: JP2011-181748A

SUMMARY OF INVENTION

Technical Problem

However, when the vinylidene fluoride/tetrafluoroethylene copolymer film disclosed in PTL 13 is used as the transparent piezoelectric film in the touch panel disclosed in PTL 12 in combination with a display, the obtained image quality is not very high as described above, in spite of the fact that the film has substantially no anisotropy and has few scratches on the surface. It has been revealed that this film deteriorates the quality of video or still images formed by display elements.

Therefore, an object of the present invention is to provide a polarized vinylidene fluoride/tetrafluoroethylene copolymer resin film that can significantly reduce, when used as an optical film, the deterioration of the quality of video or still images formed by display elements.

Another object of the present invention is to provide a production method and a production apparatus that allow the production of polarized resin films (particularly, polarized ferroelectric resin films) that have very few spot defects.

Solution to Problem

The present inventors searched for the cause of the deterioration of the quality of video or still images from various possibilities, and finally found that the cause was attributable to projections (also referred to as "spot defects" in the present specification) formed from the vinylidene fluoride/tetrafluoroethylene copolymer itself by a corona treatment.

Further, the present inventors found that the spot defects were formed due to the presence of air between the ground electrode and the non-polarized resin film (e.g., a vinylidene fluoride/tetrafluoroethylene copolymer resin film) directly placed on the ground electrode during the corona treatment. The present inventors also found that the formation of the spot defects could be greatly reduced by performing polarization by a corona treatment using a high applied voltage after the non-polarized resin film was attached to the ground electrode by a corona treatment using a low applied voltage. As a result of further research, the present invention has been completed.

That is, the present invention includes the following embodiments.

Item 1. A polarized vinylidene fluoride/tetrafluoroethylene copolymer resin film having 2,000 or fewer spot defects per $m^2$, the number of spot defects being measured by a defect measurement method;

the defect measurement method comprising reading defects of the film, using an surface inspection system in which a CCD camera is placed so as to detect defects at an angle of 45 degrees relative to an LED light source, within a rectangular range of 300 mm in a width direction, which is a direction perpendicular to a scanning direction, and 150 mm in a machine direction, which is the scanning direction, while the film is scanned under the camera at a rate of 20 m/min;

wherein, first, defects having a bright area of 1.5 $mm^2$ or less and a dark area of 1.4 $mm^2$ or less are selected; and next, in order to remove defects resulting from causes other than a corona treatment from the selected defects, a circumscribed rectangle of defect is set so as to have two sides along the scanning direction, and the number of only defects that having a circumscribed width of 2.88 mm or less, a circumscribed length of 0.43 to 2.30 mm, an aspect ratio of −39 to +27, an occupancy area ratio in the circumscribing rectangle of 4,000 to 6,950, and an area ratio of −3,100 to +5,200, is automatically counted as spot defects by the surface inspection system.

Item 2. The polarized vinylidene fluoride/tetrafluoroethylene copolymer resin film according to Item 1, wherein the number of spot defects per m$^2$ is 2,000 or fewer.

Item 3. A method for producing a polarized resin film, comprising:

step A of charging a non-polarized resin film directly placed on a ground electrode by a corona treatment using a first electrode while applying a voltage between the first electrode and the ground electrode, thereby attaching the non-polarized resin film to the ground electrode by static electricity; and step B of polarizing the non-polarized resin film attached to the ground electrode by a corona treatment using a second electrode while applying a voltage between the second electrode and the ground electrode.

Item 4. The production method according to Item 3, wherein step A is carried out while the non-polarized resin film directly placed on the ground electrode is moved relative to the first electrode, and the first electrode comprises a plurality of needle electrodes arranged perpendicular to the moving direction.

Item 5. The production method according to Item 3 or 4, wherein the non-polarized resin film is an odd-chain nylon film or a polyvinylidene fluoride-based resin.

Item 6. The production method according to Item 3 or 4, wherein the non-polarized resin film is a polyvinylidene fluoride-based resin.

Item 7. The production method according to Item 6, wherein the polyvinylidene fluoride-based resin is a vinylidene fluoride/tetrafluoroethylene copolymer resin film.

Item 8. An apparatus for producing a polarized resin film, comprising a first electrode and a second electrode;

wherein the first electrode is provided to face a ground electrode to be moved, and generates a corona discharge upon a voltage applied between the first electrode and the ground electrode, thereby charging a non-polarized resin film placed on the ground electrode so that the non-polarized resin film is attached to the ground electrode by static electricity; and the second electrode is provided downstream of the first electrode to face the ground electrode, and generates a corona discharge upon a voltage applied between the second electrode and the ground electrode, thereby polarizing the non-polarized resin film attached to the ground electrode.

Item 9. The production apparatus according to Item 8, wherein the first electrode comprises a plurality of needle electrodes arranged at predetermined intervals perpendicular to the moving direction of the ground electrode.

Item 10. The production apparatus according to Item 9, wherein the plurality of needle electrodes are arranged at intervals that are set so that a charged area of the non-polarized resin film that can be charged by a corona discharge overlaps at least part of a charged area of the non-polarized resin film charged by an adjacent needle electrode.

Item 11. The production apparatus according to any one of Items 7 to 9, wherein the second electrode comprises a wire electrode extending perpendicular to the moving direction.

Item 12. The polarized vinylidene fluoride/tetrafluoroethylene copolymer resin film according to Item 1 or 2, which is for touch panels.

Item 13. A touch panel having the polarized vinylidene fluoride/tetrafluoroethylene copolymer resin film according to Item 1 or 2.

Advantageous Effects of Invention

The polarized vinylidene fluoride/tetrafluoroethylene copolymer resin film of the present invention can significantly reduce, when used as an optical film, the deterioration of the quality of video or still images formed by display elements.

The production method of the present invention can produce a polarized vinylidene fluoride/tetrafluoroethylene copolymer resin film that can significantly reduce, when used as an optical film, the deterioration of the quality of video or still images formed by display elements.

Furthermore, the production method of the present invention can produce a polarized resin film having reduced scratches on the surface, and having substantially no anisotropy.

DESCRIPTION OF EMBODIMENTS

Figure 1:
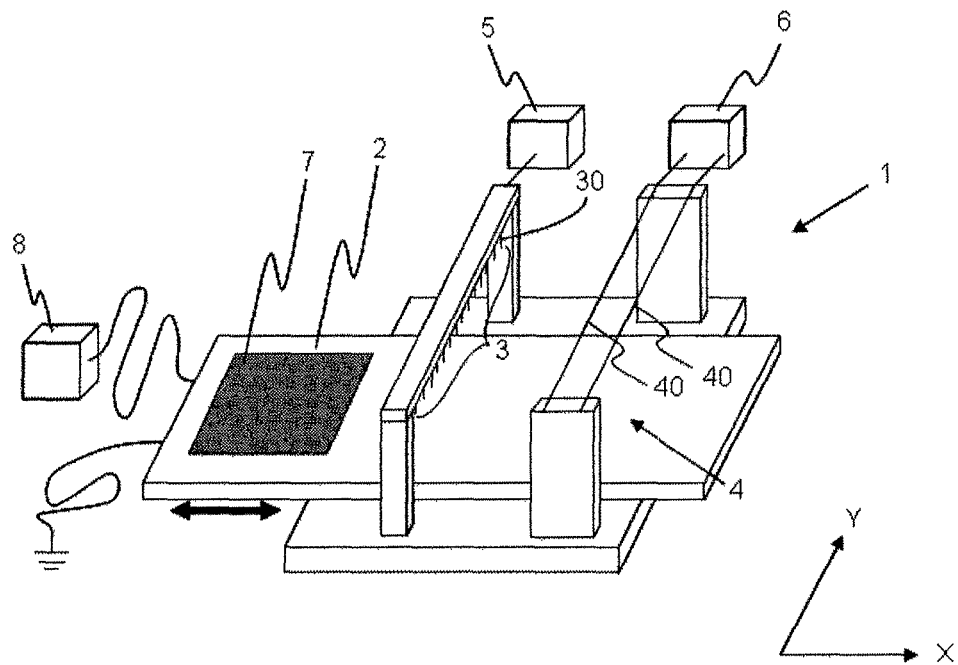
FIG. 1 is a perspective view showing the outline of the production method of the present invention and a production apparatus used in the method.

The terms used in the present specification are described below.

In the present specification, the term "anisotropy" is used with the intended meaning of the in-plane anisotropy of a film. That is, for example, a film having "no anisotropy" means that the film has no in-plane anisotropy, rather than that the film has no anisotropy in the film thickness direction.

In the present specification, the "detection" of "touch position" means the determination of the touch position. In contrast, the "detection" of "touch pressure" means the determination of the presence, speed, and intensity (strength) of pressing, the changes thereto, or a combination thereof.

In the present specification, the term "touch" includes touching, being touched, pressing, being pressed, and contacting.

1. Polarized Vinylidene Fluoride/Tetrafluoroethylene Copolymer Resin Film

The "polarized vinylidene fluoride/tetrafluoroethylene copolymer resin film" of the present invention may be a surface-charged vinylidene fluoride/tetrafluoroethylene copolymer resin film. Here, the "surface-charged vinylidene fluoride/tetrafluoroethylene copolymer resin film" is a vinylidene fluoride/tetrafluoroethylene copolymer resin film having a charged surface, that is, an electret.

Further, the "polarized vinylidene fluoride/tetrafluoroethylene copolymer resin film" of the present invention is preferably a piezoelectric vinylidene fluoride/tetrafluoroethylene copolymer resin film.

Moreover, the "polarized vinylidene fluoride/tetrafluoroethylene copolymer resin film" of the present invention is preferably a ferroelectric vinylidene fluoride/tetrafluoroethylene copolymer resin film. Here, the term "ferroelectric" means the capability of maintaining polarization even if there is no external electric field.

In the present invention, the "vinylidene fluoride/tetrafluoroethylene copolymer resin film" is a resin film formed from a vinylidene fluoride/tetrafluoroethylene copolymer.

The "vinylidene fluoride/tetrafluoroethylene copolymer resin film" may contain, in addition to a vinylidene fluoride/tetrafluoroethylene copolymer, additives that are generally used in resin films.

The vinylidene fluoride/tetrafluoroethylene copolymer may contain repeating units derived from monomers other than vinylidene fluoride and tetrafluoroethylene, unless the characteristics of the present invention are remarkably impaired. The content of such repeating units is generally 10 mol % or less. Such monomers are not limited as long as they can be copolymerized with the vinylidene fluoride monomer and the tetrafluoroethylene monomer. Examples of such monomers include:

(1) fluoromonomers (e.g., vinyl fluoride (VF), trifluoroethylene (TrFE), hexafluoropropene (HFP), 1-chloro-1-fluoro-ethylene (1,1-CFE), 1-chloro-2-fluoro-ethylene (1,2-CFE), 1-chloro-2,2-difluoroethylene (CDFE), chlorotrifluoroethylene (CTFE), trifluorovinyl monomer, 1,1,2-trifluorobutene-4-bromo-1-butene, 1,1,2-trifluorobutene-4-silane-1-butene, perfluoroalkyl vinyl ether, perfluoromethyl vinyl ether (PMVE), perfluoropropylvinyl ether (PPVE), perfluoroacrylate, 2,2,2-trifluoroethyl acrylate, and 2-(perfluorohexyl)ethyl acrylate); and (2) hydrocarbon-based monomers (e.g., ethylene, propylene, maleic acid anhydride, vinyl ether, vinyl ester, allyl glycidyl ether, acrylic acid-based monomers, methacrylic acid-based monomers, and vinyl acetate).

The thickness of the "polarized vinylidene fluoride/tetrafluoroethylene copolymer resin film" of the present invention is generally 1 to 200 µm, preferably 1 to 100 µm, and more preferably 1 to 50 µm.

The thickness is preferably thinner in tetras of transparency. When piezoelectric properties are considered important, the thickness is preferably thicker. For this reason, the thickness of the "polarized vinylidene fluoride/tetrafluoroethylene copolymer resin film" of the present invention can be suitably determined depending on the application, etc.

In the polarized vinylidene fluoride/tetrafluoroethylene copolymer resin film of the present invention, the number of spot defects per $m^2$ measured by the below-mentioned defect measurement method is 2,000 or fewer, preferably 1,560 or fewer, more preferably 1,500 or fewer, still more preferably 560 or fewer, even more preferably 240 or fewer, and particularly preferably 50 or fewer.

Thereby, the polarized vinylidene fluoride/tetrafluoroethylene copolymer resin film of the present invention can significantly reduce, when used as an optical film, the deterioration of the quality of video or still images formed by display elements.

Defect Measurement Method

Using an surface inspection system in which a CCD camera is placed so as to detect defects at an angle of 45 degrees relative to an LED source (constant current drive; continuous lighting type; light intensity: 50% (light intensity can be controlled almost linearly from 1 to 100%; 60,000 Lux at 100% output)), defects of the film are read within a rectangular range of 300 mm in the width direction (the direction perpendicular to the scanning direction) and 150 mm in the machine direction (the scanning direction), while the film is scanned under the camera at a rate of 20 m/min.

More specifically, the method uses an surface inspection system equipped with a CCD camera (having a linear actual field of view with a length of 596 mm, a scanning direction resolution of 0.040 mm/scan, and an actual field-of-view width direction resolution of 0.088 mm/pixel), a slit, and a white LED light source. The CCD camera is placed in the traveling direction of the light from the white LED light source through the slit so as to receive the light, with the length direction of the actual field of view coinciding with the direction in which the slit faces. While the film to be examined is moved in its longitudinal direction at a rate of 20 m/min between the slit and the CCD camera, the CCD camera receives the light from the white LED light source through the film to be examined, thereby scanning the film within a rectangular range of 300 mm in the width direction of the film (the direction perpendicular to the scanning direction) and 150 mm in the machine direction (the scanning direction). In this case, the film to be examined is placed so that the traveling direction of the light from the white LED light source is inclined at 45 degrees from the direction perpendicular to the plane of the film toward the longitudinal direction of the film. The longitudinal direction of the film coincides with the machine direction (the scanning direction).

First, portions having a bright area of 1.5266 $mm^2$ or less, a dark area of 1.416 $mm^2$ or less, and a total of the bright area and the dark area (hereinafter referred to as the "total area") of 2.3987 $mm^2$ or less, are selected as defects.

The bright area is the area of bright portions brighter than the background (i.e., the portion having no spot defects or other defects, such as scratches).

The dark area is the area of dark portions darker than the background.

Here, the image level of the CCD camera is confirmed by the waveform, and lighting is controlled so that the background is gray with a brightness of 5, which is regarded as 0.

When the range from brightness 5 to brightness 10 (pure white) is divided into 127, and the threshold is set as 65/127, the bright portion is a portion having a brightness exceeding the threshold (i.e., brighter).

When the range from brightness 5 to brightness 0 (pure black) is divided into 127, and the threshold is set as 100/127, the dark portion is a portion having a darkness exceeding the threshold (i.e., darker).

Next, in order to remove defects (e.g., scratches) resulting from causes other than the corona treatment contained in these defects, a circumscribed rectangle of defect is set so as to have two sides along the scanning direction, and the number of only the following defects is automatically counted as spot defects by the surface inspection system. That is, the counted defects have a circumscribed width of 2.88 mm or less, a circumscribed length of 0.43 to 2.30 mm, an aspect ratio of −39 to +27, an occupancy area ratio in the circumscribing rectangle of 4,000 to 6,950, and an area ratio of −3,100 to +5,200.

The surface inspection system used is MaxEye.Impact (trade name, Futec, Inc.), or an surface inspection system by which the same measurement results as the MaxEye.Impact can be obtained in the above defect measurement method.

The meaning of the teens "circumscribed width," "circumscribed length," "aspect ratio," "occupancy area ratio," and "area ratio" used herein is as follows.

The "circumscribed width" is defined as the size of a defect in the direction (crosswise) perpendicular to the scanning direction, i.e., the width of the rectangle circumscribing the defect.

The "circumscribed length" is defined as the size of a defect in the scanning direction (lengthwise), i.e., the length of the rectangle circumscribing the defect.

The "aspect ratio" is the ratio of the circumscribed length and circumscribed width of a defect. In the present invention, the aspect ratio is defined as a value obtained by dividing the larger value between the circumscribed length and the circumscribed width by the smaller value. When the circumscribed length is larger, a positive sign (+) is given to the quotient; whereas when the circumscribed width is larger, a negative sign (−) is given to the quotient.

The "occupancy area ratio" is defined as the ratio of the total area (total area of bright portions and dark portions) to the rectangle circumscribing the defect.

The "area ratio" is the ratio of the bright area to the dark area in the defect determination part. In the present invention, the area ratio is defined as a value obtained by subtracting the dark area from the bright area, and then dividing the resulting value by the total area. Accordingly, when the area ratio value is a positive number, the defects are bright defects; whereas when the area ratio value is a negative number, the defects are dark defects.

When MaxEye.Impact (trade name, Futec, Inc.) is used, the measurement is performed specifically with the following parameters:
Brightness
[LP]
Maximum value: 127
Minimum value: 65
[DP]
Maximum value: 127
Minimum value: 100
Bright area
[LA]
Maximum value: 1.5266
Dark area
[DA]
Maximum value: 1.4161
Total area
Maximum value: 2.3987
Width
[W]
Maximum value: 2.88
Length
[L]
Maximum value: 2.30
Minimum value: 0.43

Portions whose measurement results satisfy all of the following conditions (1) to (10) are counted as spot defects.
(1) $65<LP$
(2) $100<DP$
(3) $LA \leq 1.5266$
(4) $DA \leq 1.4161$
(5) $A \leq 2.3987$
(6) $W<2.88$
(7) $0.43<L<2.30$
(8) $-39<R1<+27$
(wherein when $W>L$, $R1=W/L \times (-1)$; and when $W<L$, $R1=L/W$)
(9) $4,000 \leq R2 \leq 6,950$
(wherein $R2=A/(W \times L) \times 10,000$)
(10) $-3,100 \leq R3 \leq 5,200$
(wherein $R3=(LA-DA)/A \times 10,000$)

The polarized vinylidene fluoride/tetrafluoroethylene copolymer resin film of the present invention can be produced by a method for producing a polarized resin film, described below.

2. Method for Producing Polarized Resin Film

The method for producing a polarized resin film (particularly a polarized ferroelectric resin film) according to the present invention comprises:

step A of charging a non-polarized resin film directly placed on a ground electrode by a corona treatment using a first electrode while applying a voltage between the first electrode and the ground electrode, thereby attaching the non-polarized resin film to the ground electrode by static electricity; and step B of polarizing the non-polarized resin film attached to the ground electrode by a corona treatment using a second electrode while applying a voltage between the second electrode and the ground electrode.

2.1. Step A

In step A, a non-polarized resin film directly placed on a ground electrode is charged by a corona treatment using a first electrode while applying a voltage between the first electrode and the ground electrode, thereby attaching the non-polarized resin film to the ground electrode by static electricity.

Examples of the non-polarized resin film include odd-chain nylon films, polyvinylidene fluoride-based resins, and the like.

Examples of odd-chain nylon films include Nylon 11 and the like.

Examples of polyvinylidene fluoride-based resins include polyvinylidene fluoride resin films having a p-type crystal structure (type-I crystal structure) after being stretched; copolymer resin films of vinylidene fluoride and other monomers that can be copolymerized with vinylidene fluoride containing 50 mol % or more (preferably 70 mol % or more) of vinylidene fluoride; and the like.

Other monomers that can be copolymerized with vinylidene fluoride are, for example, one or more members selected from the group consisting of trifluoroethylene, tetrafluoroethylene, hexafluoropropylene, ethylene chloride trifluoride, vinyl fluoride, and the like.

The non-polarized resin film used in the present invention is preferably a polyvinylidene fluoride-based resin, and particularly preferably a vinylidene fluoride/tetrafluoroethylene copolymer.

The resin film used in step A can be produced by, for example, casting using a polymer solution, heat pressing, molten extrusion, or other known methods. The resin film used in step A is preferably an unstretched film. It is also preferable, in the production method of the present invention, that the non-polarized resin film is not stretched. Thereby, the production method of the present invention can produce a film that has reduced scratches on the surface and has substantially no anisotropy.

The "non-polarized resin film" used in step A may be heated after film production.

The method of heat treatment is not particularly limited. For example, the heat treatment can be performed by holding the resin film between two metal plates, and heating the metal plates; or by heating a roll of the resin film in a thermostat. Alternatively, when the resin film is produced by a roll-to-roll process, the heat treatment can be performed by heating a metal roll, and bringing the resin film into contact with the heated metal roll. The abovementioned ground electrode can also serve as the metal plate.

The heat treatment can improve the degree of crystallinity, and increase the piezoelectric properties. The temperature of the heat treatment ranges from, for example, the melting point of the polymer constituting the resin film −100° C. to the melting point of the polymer constituting the resin film +50° C. When the resin film is heated to a temperature higher than the melting point of the polymer constituting the resin film, it is preferable to slowly cool the resin film after heating. When the resin film is heated to a temperature lower than the melting point of the polymer constituting the resin film, it is preferable to keep heating.

Moreover, the heat treatment can reduce the residual stress of the non-polarized resin film, and reduce defamation, such as shrinkage, due to heating. The heating temperature in this case is lower than the melting point.

Furthermore, in terms of maintaining the transparency of the non-polarized resin film, it is preferable to perform heat treatment at a temperature lower than the melting point.

The time for the heat treatment is generally 240 hours or less, although it depends on the amount (volume, weight) of the non-polarized resin film. Short-time heating can be performed, for example, by bringing the resin film into contact with a heated roll.

After heat treatment, the non-polarized resin film is cooled to a predetermined temperature before step A, if desired. This temperature is preferably 0° C. to 50° C., and the cooling rate is preferably 15° C./min to 0.5° C./min.

The thickness of the non-polarized resin film used in step A may be the same as the thickness of the polarized resin film to be obtained.

For the corona discharge, either a negative corona or a positive corona can be used; however, a negative corona is preferably used because of the ease with which the non-polarized resin film can be charged.

As a result of the charging, the non-polarized resin film is attached to the ground electrode by static electricity.

It is preferable that, as a result of the charging, the non-polarized resin film be attached to the ground electrode by static electricity so that air between the non-polarized resin film and the ground electrode is pushed out.

Air between the non-polarized resin film and the ground electrode can be pushed out by, for example, continuously performing a corona treatment from one end of the non-polarized resin film to the other end of the opposite side. This allows the non-polarized resin film to be continuously attached to the ground electrode from the end of the film, thereby pushing out the air.

Therefore, step A is preferably carried out while moving the non-polarized resin film directly placed on the ground electrode relative to the first electrode. The speed of this movement is also referred to as the processing speed of step A. This movement can be achieved by, for example, moving the ground electrode and/or the first electrode so that the position of the non-polarized resin film to undergo a corona treatment is changed.

The first electrode can be, for example, a needle electrode or a wire electrode, but is preferably a needle electrode.

When the first electrode is a needle electrode, the first electrode comprises a plurality of needle electrodes arranged perpendicular to the moving direction. The plurality of needle electrodes may be arranged almost perpendicular in the moving method, and can be placed in a single line or in plural lines.

The plurality of needle electrodes are preferably placed so that the non-polarized resin film can be charged without space. That is, the plurality of needle electrodes are preferably arranged within a certain distance. Specifically, the distance is, for example, less than 1.5 cm or less than 1.2 cm, although it varies depending on the shape of the needle electrodes, the distance between the needle electrodes and the non-polarized resin film, the voltage applied to the needle electrodes, etc. When the voltage is high, the distance can be longer.

Because such electrodes are used as the first electrode, the air is easily pushed out by the continuous corona treatment from one end of the non-polarized resin film to the other end of the opposite side, and the remaining air can be highly suppressed. This is presumably because the air is easily pushed out (the air easily escapes) due to the non-linear shape of the end of the part of the non-polarized resin film attached to the ground electrode; however, the present invention is not limited thereto.

The conditions for the corona treatment in step A are set so as to be suitable for the charging of the non-polarized resin film.

Although a corona treatment is also performed in step B, described later, the corona treatment in step A is performed under milder conditions than those of step B. Specifically, for example, when the corona treatment (charging treatment) in step A is compared with the corona treatment (polarization treatment) in step B, the surface potential of the film after the treatment satisfies step A (charging treatment) <step B (polarization treatment). For example, when the distance from the electrode to the object (film) is the same, the applied voltage satisfies step A (charging treatment)<step B (polarization treatment). Moreover, when the applied voltage from the electrode to the object (film) is the same, the distance from the electrode to the object (film) satisfies step A (charging treatment)>step B (polarization treatment).

When the conditions are overly mild, charging is insufficient, and air remains between the non-polarized resin film and the ground electrode. As a result, spot defects may be formed in the finally obtained polarized resin film. In contrast, when the conditions are overly severe, defects due to the corona treatment are formed on the non-polarized resin film. As a result, spot defects may remain in the finally obtained polarized resin film.

Examples of factors of such conditions for the corona treatment include the voltage applied between the first electrode and the ground electrode, the distance between the first electrode and the non-polarized resin film, and the processing speed of step A.

Among these factors, when the conditions include a severe factor, other factors may be mild so as to make the conditions comprehensively suitable for the corona treatment.

The stronger the voltage applied between the first electrode and the ground electrode, the more severe the conditions for the corona treatment in step A. The voltage is specifically, for example, −5 to −15 kV.

The distance between the first electrode and the non-polarized resin film is substantially the same as the distance between the first electrode and the ground electrode. The shorter the distance, the more severe the conditions for the corona treatment in step A. The distance is specifically, for example, 1 to 50 mm or 5 to 15 mm.

The slower the processing speed of step A, the more severe the conditions for the corona treatment in step A. The processing speed of step A is specifically, for example, 10 to 500 cm/min. The speed varies depending on the shape of the first electrode, etc. For example, when the first electrode comprises wire electrodes, the more the number of wire electrodes, the faster the speed.

2.2. Step B

In step B, the non-polarized resin film attached to the ground electrode is polarized by a corona treatment using a second electrode while applying a voltage between the second electrode and the ground electrode.

For the corona discharge, either a negative corona or a positive corona can be used; however, a negative corona is preferably used because of the ease with which the non-polarized resin film is polarized.

Step B is carried out while the non-polarized resin film is attached to the ground electrode by step A.

Step B is preferably carried out while moving the non-polarized resin film directly placed on the ground electrode relative to the second electrode. The speed of this movement is also referred to as the processing speed of step B. This movement can be achieved by, for example, moving the ground electrode and/or the second electrode so that the position of the non-polarized resin film to undergo a corona treatment is changed.

In the above step A, when the corona treatment is performed continuously from one end of the non-polarized resin film to the other end of the opposite side, the corona treatment in step B can be started from the one end before the corona treatment in step A reaches the other end of the opposite side.

The second electrode can be, for example, a needle electrode or a wire electrode.

When the second electrode is a wire electrode, the wire electrode is placed perpendicular to the moving direction of the non-polarized resin film. The number of second electrodes may be singular or plural (e.g., two). In terms of completely polarizing the non-polarized resin film at a relatively low voltage, the number of wire electrodes is preferably plural. Specifically, for example, two wire electrodes are preferred.

The formation of spot defects on the non-polarized resin film caused by a high voltage can be reduced by polarizing the film at a relatively low voltage.

When the second electrode is a needle electrode, the second electrode comprises a plurality of needle electrodes arranged perpendicular to the moving direction. The plurality of needle electrodes may be arranged almost perpendicular in the moving method, and can be placed in a single line or in plural lines (i.e., one-dimensionally or two-dimensionally).

The plurality of needle electrodes are preferably placed so that the non-polarized resin film can be polarized without space. That is, the plurality of needle electrodes are preferably arranged within a certain distance. Specifically, the distance is, for example, less than 1.5 cm or less than 1.2 cm, although it varies depending on the shape of the needle electrodes, the distance between the needle electrodes and the non-polarized resin film, the voltage applied to the needle electrodes, etc. When the voltage is high, the distance can be longer.

The conditions for the corona treatment in step B are set so as to be suitable for the polarization of the non-polarized resin film.

As can be understood from the description of step A, the corona treatment in step B is performed under more stringent conditions than those of step A.

When the conditions are overly mild, polarization is insufficient. In contrast, when the conditions are overly severe, spot defects due to the corona treatment are formed on the non-polarized resin film.

Examples of factors of such conditions include the voltage applied between the second electrode and the ground electrode, the distance between the second electrode and the non-polarized resin film, and the processing speed of step B.

Among these factors, when the conditions include a severe factor, other factors may be mild so as to make the conditions comprehensively suitable for the corona treatment.

The stronger the voltage applied between the second electrode and the ground electrode, the more severe the conditions for the corona treatment in step B. The voltage varies depending on the distance between the second electrode and the non-polarized resin film, but is specifically, for example, −15 to −25 kV.

The distance between the second electrode and the non-polarized resin film is substantially the same as the distance between the second electrode and the ground electrode. The shorter the distance, the more severe the conditions for the corona treatment in step B. The distance is specifically, for example, 1 to 50 mm, and preferably 10 to 25 mm.

The slower the processing speed of step B, the more severe the conditions for the corona treatment in step B. The processing speed of step B is, for example, 10 to 500 cm/min. The speed varies depending on the shape of the second electrode, etc. For example, when the second electrode comprises wire electrodes, the more the number of wire electrodes, the faster the speed.

The temperature of the non-polarized resin film during the corona treatment in step B is preferably 20° C. to 120° C., and more preferably 20° C. to 85° C. By discharging while heating during polarization, heat resistance of the applied charge, and piezoelectric properties can be improved.

The polarized vinylidene fluoride/tetrafluoroethylene copolymer resin film of the present invention can significantly reduce, when used as an optical film, the deterioration of the quality of video or still images formed by display elements, and can be suitably used as an optical film.

Moreover, the polarized resin film produced by the production method of the present invention has substantially no anisotropy and has few scratches on the surface, and therefore can be suitably used as an optical film having piezoelectric properties.

In general, films used for optical applications preferably have a lower total haze value. Specifically, the total haze value is preferably 2.5% or less, more preferably 2% or less, and even more preferably 1% or less.

The polarized vinylidene fluoride/tetrafluoroethylene copolymer resin film of the present invention and the polarized resin film produced by the production method of the present invention can have such a total haze value.

Next, one embodiment of the production method of the present invention is described in more detail with reference to FIG. 1.

FIG. 1 shows the outline of the production apparatus used in the production method of the present invention.

The production apparatus 1 of this embodiment comprises a ground electrode 2 to be moved, a first electrode 3 provided above the ground electrode 2, and a second electrode 4 provided above the ground electrode 2 and downstream of the first electrode 3 along the moving direction of the ground electrode 2.

While the ground electrode 2 is grounded, the first electrode 3 and the second electrode 4 are connected, respectively, to a first high-voltage power supply 5 and a second high-voltage power supply 6. The first high-voltage power supply 5 applies a voltage between the first electrode 3 and the ground electrode 2, and the second high-voltage power supply 6 applies a voltage between the second electrode 4 and the ground electrode 2, thereby generating a corona discharge from the first electrode 3 and the second electrode 4 towards the ground electrode 2.

The ground electrode 2 of this embodiment has a flat upper surface, on which a non-polarized resin film 7 is directly placed. When the ground electrode 2 is moved in the direction indicated by arrow X in FIG. 1, the non-polarized resin film 7 is also moved in the same direction, and sequentially faces the first electrode 3 and the second electrode 4.

The first electrode 3 of this embodiment comprises a plurality of needle electrodes 30 arranged at predetermined intervals in the direction Y perpendicular to the moving direction X of the ground electrode 2. Each needle electrode 30 has a needle-like shape with a sharpened tip so as to effectively generate a corona discharge. Each needle electrode 30 is made of, for example, aluminum, stainless steel, tungsten, or tantalum, and its surface may be plated with gold, etc. The tip of each needle electrode 30 faces the ground electrode 2. The needle electrodes 30 are provided so that they can sufficiently cover the width of the non-polarized resin film 7 in the perpendicular direction Y. In FIG. 1, the plurality of needle electrodes 30 are provided only in a single line in the moving direction X of the ground electrode 2; however, the needle electrodes 30 may be provided in several lines. Moreover, the plurality of needle electrodes 30 may be arranged almost perpendicular to the moving direction X of the ground electrode 2.

The second electrode 4 of this embodiment comprises wire electrodes 40 extending in the direction Y perpendicular to the moving direction X of the ground electrode 2. The wire electrodes 40 are made of, for example, aluminum, stainless steel, tungsten, or tantalum, and their surface may be plated with gold, etc. The wire electrodes 40 extend in parallel above the ground electrode 2 so that they can sufficiently cover the width of the non-polarized resin film 7 in the perpendicular direction Y. In FIG. 1, the two wire electrodes 40 are provided in the moving direction X of the ground electrode 2; however, the number of wire electrodes may be one or three or more. Moreover, the wire electrodes 40 may extend almost perpendicular to the moving direction X of the ground electrode 2.

In the production apparatus 1 having the above structure, while the ground electrode 2 is moved in the moving direction X, a voltage is applied between the first electrode 3 and the ground electrode 2 to thereby allow the first electrode 3 to generate a corona discharge, which sequentially charges the non-polarized resin film 7 on the ground electrode 2 from one end (the end on the side of the moving direction X) of the film toward the other end (the end on the opposite side of the moving direction X). The charged non-polarized resin film 7 is attached to the ground electrode 2 continuously from the one end to the other end by static electricity. In this case, air present between the ground electrode 2 and the non-polarized resin film 7 is pushed out in the direction opposite to the moving direction X, and discharged from the other end of the non-polarized resin film 7. Thus, the non-polarized resin film 7 is neatly attached to the ground electrode 2 without generating bubbles or wrinkles. Subsequently, the ground electrode 2 to which the non-polarized resin film 7 is attached is further moved in the moving direction X. A voltage is applied between the second electrode 4 and the ground electrode 2 to thereby allow the second electrode 4 to generate a corona discharge, which continuously polarizes the non-polarized resin film 7 from one end to the other end.

In the treatment to attach the non-polarized resin film 7 to the ground electrode 2 using the first electrode 3 (step A), the voltage applied between the first electrode 3 and the ground electrode 2 is, for example, about −5 to −15 kV. The distance between the first electrode 3 and the non-polarized resin film 7 is substantially the same as the distance between the first electrode 3 and the ground electrode 2. The distance is, for example, about 1 to 50 mm, and preferably 5 to 15 mm. Moreover, the moving rate of the ground electrode 2 is, for example, 10 to 500 cm/min.

Figure 2:
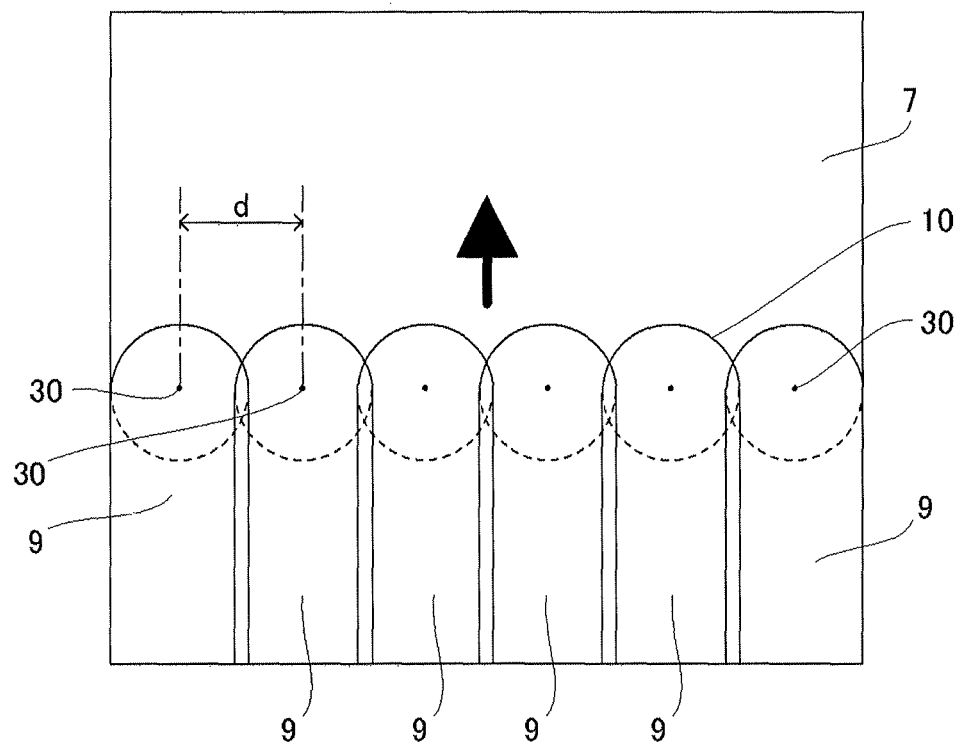
FIG. 2 is an explanatory view showing the charged areas of a vinylidene fluoride/tetrafluoroethylene copolymer resin film charged by needle electrodes.

Furthermore, the plurality of needle electrodes 30 constituting the first electrode 3 are arranged at intervals d that are set so that a charged area 9 of the non-polarized resin film that can be charged by a corona discharge overlaps at least part of a charged area 9 of the non-polarized resin film charged by the adjacent needle electrode 30, as shown in FIG. 2. Thereby, the non-polarized resin film 7 is charged by the plurality of needle electrodes 30 without space. Moreover, in this case, when the end 10 of the part of the non-polarized resin film 7 attached to the ground electrode 2 has a wavy shape, rather than a linear shape, air between the ground electrode 2 and the non-polarized resin film 7 can be easily pushed out. Thus, the remaining air can be highly suppressed.

On the other hand, in the treatment to polarize the non-polarized resin film 7 using the second electrode 4 (step B), the voltage applied between the second electrode 4 and the ground electrode 2 is, for example, about −15 to −25 kV. The distance between the second electrode 4 and the non-polarized resin film 7 is substantially the same as the distance between the second electrode 4 and the ground electrode 2. The distance is, for example, about 1 to 50 mm, and preferably 10 to 25 mm. Moreover, the moving rate of the ground electrode 2 is, for example, 10 to 500 cm/min.

The ground electrode 2 is connected to a temperature controller 8. The temperature of the non-polarized resin film 7 during voltage application can be adjusted by controlling the temperature of the ground electrode 2. It is preferable to control the temperature of the non-polarized resin film 7 during the attachment treatment in step A to be 20° C. to 120° C., and more preferably 20° C. to 85° C., by measuring the temperature of the non-polarized resin film 7 during voltage application by a thermometer (not shown), etc. Moreover, it is preferable to control the temperature of the non-polarized resin film 7 during the polarization treatment in step B to be 20° C. to 120° C., and more preferably 20° C. to 85° C. By discharging while heating during polarization, heat resistance of the applied charge, and piezoelectric properties can be improved.

The embodiment of the present invention described above is one embodiment of the present invention. The present invention is not limited to this embodiment, and can be changed or modified within a range that satisfies the requirements of the present invention and that can achieve the object and effects of the present invention. It is a matter of course that the scope of the present invention also includes such changed and modified versions.

For example, the first electrode 3 may comprise wire electrodes, and the second electrode 4 may comprise needle electrodes.

Figure 3:
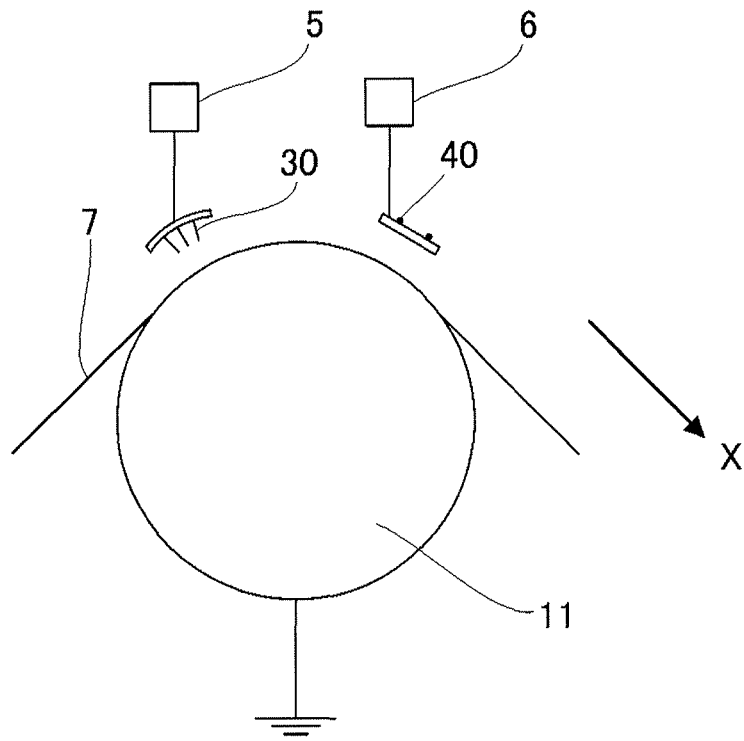
FIG. 3 is a schematic view showing the outline of another embodiment of the production method of the present invention and a production apparatus used in the method.

Moreover, the ground electrode 2 is not necessarily moved in a state where the upper surface is flat. The ground electrode 2 may be moved along a roll 11, as shown in FIG. 3.

The polarized vinylidene fluoride/tetrafluoroethylene copolymer resin film of the present invention, the polarized resin film produced by the production method of the present invention, and the polarized resin film produced using the production apparatus of the present invention (hereinafter also referred to as the resin films of the present invention) preferably have piezoelectric properties, and are suitably used in piezoelectric panels (e.g., touch panels, preferably touch panels that can detect touch pressure).

The resin film of the present invention can be used in various types of touch panels, such as resistance film-type touch panels and capacitance-type touch panels.

When the resin film of the present invention is used in a touch panel, it is not always necessary to use the film to detect both touch position and touch pressure; the piezoelectric film of the present invention may be used to detect either touch position or touch pressure.

A piezoelectric panel (e.g., a touch panel, preferably a touch panel that can detect touch pressure) having the resin film of the present invention comprises:

(1) the resin film of the present invention (preferably the polarized vinylidene fluoride/tetrafluoroethylene copolymer resin film of the present invention); and (2) a transparent electrode.

Examples of the transparent electrode include ITO (indium tin oxide) electrodes, tin oxide electrodes, and the like.

A piezoelectric panel (e.g., a touch panel, preferably a touch panel that can detect touch pressure) having the resin film of the present invention preferably comprises a first electrode, the resin film of the present invention, and a second electrode, in this order.

The first electrode is placed directly or indirectly on one main surface of the resin film of the present invention, and the second electrode is placed directly or indirectly on the other main surface of the resin film of the present invention.

The first electrode and the second electrode may be the aforementioned transparent electrodes.

When the "touch panel that can detect touch pressure" having the resin film of the present invention is pressed with a finger, or the like, electrical signals according to changes with time in the strain of the resin film of the present invention can be obtained; therefore, the presence, speed, and intensity (strength) of pressing, their changes, or a combination thereof can be determined by using the "touch panel that can detect touch pressure." The intensity of pressing (i.e., static pressure) can be determined using the integral value of the electrical signals.

In such a piezoelectric panel, one or more (preferably two) resin films of the present invention can be used.

When two or more (preferably two) resin films of the present invention are used, the two or more resin films of the present invention may be attached to each other by an adhesive sheet. The adhesive sheet is not particularly limited, as long as the resin films of the present invention can be attached to each other. The adhesive sheet may comprise one or more layers. That is, when the adhesive sheet comprises one layer, the adhesive sheet comprises an adhesive layer; and when the adhesive sheet comprises two or more layers, both outer layers are adhesive layers. When the adhesive sheet comprises three or more layers, the adhesive sheet may have a base material layer as an internal layer.

For example, the adhesive layer may preferably be a layer containing an acrylic adhesive as the adhesive.

The base material layer is preferably a transparent film, such as polyimide, polyethylene terephthalate, polybutylene terephthalate, polycarbonate, polyparaphenylene sulfide, or polyamideimide.

For example, a piezoelectric panel (e.g., a touch panel, preferably a touch panel that can detect touch pressure) having the resin film of the present invention preferably comprises a first electrode, the first resin film of the present invention, an adhesive sheet, the second resin film of the present invention, and a second electrode, in this order.

The first electrode is placed on the outer surface of the first resin film of the present invention, and the second electrode is placed on the outer surface of the second resin film of the present invention.

The resin film of the present invention may have pyroelectric properties. In such a piezoelectric panel, when the first resin film of the present invention and the second resin film of the present invention are placed so that the surface of each film on which the same polar charge (e.g., positive charge and positive charge) is generated by temperature increases faces the outside, and when the electric potential difference between the two surfaces is obtained as electrical signals by the first electrode and the second electrode, electrical signals due to the piezoelectric properties can be selectively obtained while electrical signals due to the pyroelectric properties are reduced.

Such a touch panel can be used in touch input devices and touch sensor devices. An input device having the touch panel (i.e., an input device having the piezoelectric film of the present invention) allows inputs based on touch position, touch pressure, or both of them (e.g., an input based on the intensity (strength) of pressing, such as writing pressure). The input device having the touch panel may have a position detector and a pressure detector.

The touch panel of the present invention (preferably a touch panel having a polarized vinylidene fluoride/tetrafluoroethylene copolymer resin film) can be used in electronic devices. Examples of the electronic devices include smartphones, tablet PCs, digitizers, touch pads, car-navigation systems, and the like. Such an electronic device allows operations based on touch position, touch pressure, or both of them (e.g., an operation in paint software to change the thickness of a line displayed on the screen according to writing pressure).

The electronic device may be equipped with a touch input device or a touch sensor device, or may consist of a touch input device or a touch sensor device. The touch input device and the touch sensor device each comprise the touch panel of the present invention.

EXAMPLES

The present invention is described in more detail below with reference to Examples; however, the present invention is not limited thereto.

The electrodes used in the following Examples and Comparative Examples were as follows.
Electrodes (1) A needle electrode rod in which electrode needles (needle electrodes) (R=0.06 mm; produced by Morita Seishinsyo Co., Ltd.) were arranged in a line at intervals of 10 mm on the centerline of a brass rod having a width of 20 mm (thickness: 10 mm, length: 500 mm)

(2) A needle electrode rod in which electrode needles (R=0.06 mm; produced by Morita Seishinsyo Co., Ltd.) were arranged in a line at intervals of 15 mm, as with the needle electrode rod (1)

(3) A tungsten wire electrode (length: 500 mm) plated with gold and having a diameter of 0.1 mm In the following Examples and Comparative Examples, the total light transmission, total haze value, electromechanical coupling coefficient, and spot defects of films were measured by the methods described below.
Total Light Transmission The total light transmission was measured according to the method described in ASTM D1003 using a Haze Guard II (trade name, Toyo Seiki Seisaku-sho, Ltd.).

Total Haze Value

The total haze value was measured according to the method described in ASTM D1003 using a Haze Guard II (trade name, Toyo Seiki Seisaku-sho, Ltd.).

Electromechanical Coupling Coefficient

Al-evaporated electrodes were formed on both sides of a transparent piezoelectric film. A 13-mm disc was cut from a predetermined part of the transparent piezoelectric film, and subjected to measurement using an impedance analyzer (4194A, produced by Hewlett Packard). Then, the electromechanical coupling coefficient was calculated by the method described in "The application of ferroelectric polymer and ultrasonic transducers in the megahertz range" (H. Ohigashi, et al.).

Spot Defects

Spot defects were detected by the following method, and their number was counted.

Defect Measurement Method

Using an surface inspection system in which a CCD camera is placed so as to detect defects at an angle of 45 degrees relative to an LED source (constant current drive; continuous lighting type; light intensity: 50% (light intensity can be controlled almost linearly from 1 to 100%; 60,000 Lux at 100% output)), defects of a film are read within a rectangular range of 300 mm in the width direction (the direction perpendicular to the scanning direction) and 150 mm in the machine direction (the scanning direction), while the film is scanned under the camera at a rate of 20 m/min.

Figure 4:
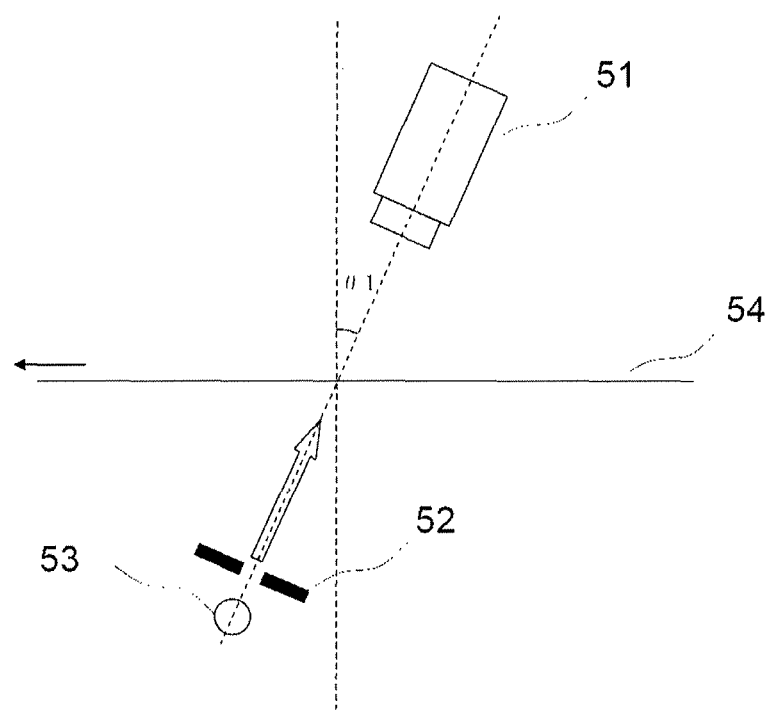
FIG. 4 is an explanatory view of the film defect measurement method used in the present invention.

This method is described in more detail with reference to FIG. 4. More specifically, the method uses an surface inspection system equipped with a CCD camera 51 (having a linear actual field of view with a length of 596 mm, a scanning direction resolution of 0.040 mm/scan, and an actual field-of-view width direction resolution of 0.088 mm/pixel), a slit 52, and a white LED light source 53. The CCD camera 51 is placed in the traveling direction (indicated by the white arrow in FIG. 4) of the light from the white LED light source 53 through the slit 52 so as to receive the light, with the length direction of the actual field of view coinciding with the direction in which the slit 52 faces. While a film 54 to be examined is moved in its longitudinal direction at a rate of 20 m/min between the slit 52 and the CCD camera 51, the CCD camera 51 receives the light from the white LED light source 53 through the film 54 to be examined, thereby scanning the film within a rectangular range of 300 mm in the width direction of the film 54 (the direction perpendicular to the scanning direction) and 150 mm in the machine direction (the scanning direction, indicated by the black arrow in FIG. 4). In this case, the film 54 to be examined is placed so that the traveling direction of the light from the white LED light source 53 is inclined at 45 degrees from the direction perpendicular to the plane of the film 54 toward the longitudinal direction of the film 54; that is, θ1 in FIG. 4 is 45 degrees. The longitudinal direction of the film 54 coincides with the machine direction (the scanning direction).

First, portions having a bright area of 1.5266 mm² or less, a dark area of 1.416 mm² or less, and a total of the bright area and the dark area (hereinafter referred to as the "total area") of 2.3987 mm² or less, are selected as defects.

The bright area is the area of bright portions brighter than the background (i.e., the portion having no spot defects or other defects, such as scratches).

The dark area is the area of dark portions darker than the background.

Here, the image level of the CCD camera is confirmed by the waveform, and lighting is controlled so that the background is gray with a brightness of 5, which is regarded as 0.

When the range from brightness 5 to brightness 10 (pure white) is divided into 127, and the threshold is set as 65/127, the bright portion is a portion having a brightness exceeding the threshold (i.e., brighter).

When the range from brightness 5 to brightness 0 (pure black) is divided into 127, and the threshold is set as 100/127, the dark portion is a portion having a darkness exceeding the threshold (i.e., darker).

Next, in order to remove defects (e.g., scratches) resulting from causes other than the corona treatment contained in these defects, a circumscribed rectangle of defect is set so as to have two sides along the scanning direction, and the number of only the following defects is automatically counted as spot defects by the surface inspection system. That is, the counted defects have a circumscribed width of 2.88 mm or less, a circumscribed length of 0.43 to 2.30 mm, an aspect ratio of −39 to +27, an occupancy area ratio in the circumscribing rectangle of 4,000 to 6,950, and an area ratio of −3,100 to +5,200.

The surface inspection system used is MaxEye.Impact (trade name, Futec, Inc.), or an surface inspection system by which the same measurement results as the MaxEye.Impact can be obtained in the above defect measurement method.

The meaning of the terms "circumscribed width," "circumscribed length," "aspect ratio," "occupancy area ratio," and "area ratio" used herein is as follows.

The "circumscribed width" is defined as the size of a defect in the direction (crosswise) perpendicular to the scanning direction, i.e., the width of the rectangle circumscribing the defect.

The "circumscribed length" is defined as the size of a defect in the scanning direction (lengthwise), i.e., the length of the rectangle circumscribing the defect.

The "aspect ratio" is the ratio of the circumscribed length and circumscribed width of a defect. In the present invention, the aspect ratio is defined as a value obtained by dividing the larger value between the circumscribed length and the circumscribed width by the smaller value. When the circumscribed length is larger, a positive sign (+) is given to the quotient; whereas when the circumscribed width is larger, a negative sign (−) is given to the quotient.

The "occupancy area ratio" is defined as the ratio of the total area (the total area of bright portions and dark portions) to the rectangle circumscribing the defect.

The "area ratio" is the ratio of the bright area to the dark area in the defect determination part. In the present invention, the area ratio is defined as a value obtained by subtracting the dark area from the bright area, and then dividing the resulting value by the total area. Accordingly, when the area ratio value is a positive number, the defects are bright defects; whereas when the area ratio value is a negative number, the defects are dark defects.

Using MaxEye.Impact (trade name, Futec, Inc.), the measurement was performed specifically with the following parameters:

Brightness
[LP]
Maximum value: 127
Minimum value: 65
[DP]
Maximum value: 127
Minimum value: 100

Bright area
[LA]
Maximum value: 1.5266
Dark area
[DA]
Maximum value: 1.4161
Total area
Maximum value: 2.3987
Width
[W]
Maximum value: 2.88
Length
[L]
Maximum value: 2.30
Minimum value: 0.43

Portions whose measurement results satisfy all of the following conditions (1) to (10) are counted as spot defects.
(1) 65<LP
(2) 100<DP
(3) LA≤1.5266
(4) DA≤1.4161
(5) A≤2.3987
(6) W<2.88
(7) 0.43<L<2.30
(8) −39<R1<+27
(wherein when W>L, R1=W/L×(−1); and when W<L, R1=L/W)
(9) 4,000≤R2≤6,950
(wherein R2=A/(W×L)×10,000)
(10) −3,100≤R3≤5,200
(wherein R3=(LA−DA)/A×10,000)

Using the MaxEye.Impact surface inspection system (produced by Futec, Inc.), the number of spot defects in a predetermined range of the polarized film was counted.

Specifically, the CCD camera was placed so as to detect defects at an angle of 45 degrees relative to the LED source, defects of the film were read within a rectangular range of 300 mm in the width direction (the direction perpendicular to the scanning direction) and 150 mm in the machine direction (the scanning direction), while the film was scanned under the camera at a rate of 20 m/min.

First, portions having a bright area of 1.5 mm² or less, and a dark area of 1.4 mm² or less, which corresponded to a flicker of light reflecting from the film surface when spot defects were visually observed, were selected as defects.

Next, in order to remove defects resulting from causes other than the corona treatment contained in these defects, a circumscribed rectangle of defect was set so as to have two sides along the scanning direction, and the number of only the following defects was counted as spot defects. That is, the counted defects had a circumscribed width of 2.88 mm or less, a circumscribed length of 2.30 mm or less, an aspect ratio of −39 to +27, an occupancy area ratio in the circumscribing rectangle of 4,000 to 6,950, and an area ratio of −3,100 to +5,200.

Production Example 1 (Production of Resin Film)

A 40-μm-thick vinylidene fluoride-tetrafluoroethylene copolymer film (molar ratio=80:20) was produced by the following method.

A dimethylacetamide (DMAc) solution of a vinylidene fluoride-tetrafluoroethylene copolymer (molar ratio=80:20) or a methyl ethyl ketone (MEK) solution was cast on a PET (polyethylene terephthalate) substrate, and the solvent was evaporated at 180° C., thereby molding a 40-μm-thick film.

The film was used after it was peeled from the PET substrate and then cut into a suitable size.

Example 1

As shown in the outline in FIG. 1, a 40-μm-thick vinylidene fluoride/tetrafluoroethylene copolymer resin film cut into a size of 320 mm×230 mm (hereinafter simply referred to as the "film") was placed on an SUS ground electrode (300 mm×210 mm) having a flat upper surface and being horizontally movable. As the first electrode, the needle electrodes (1) were disposed so that the line of the needle electrodes was perpendicular to the moving direction of the ground electrode, and so that the tips of the needle electrodes were located 10 mm above and apart from the film. Further, as the second electrode, tungsten wire electrodes (length: 500 mm) having a diameter of 0.1 mm and plated with gold were disposed at positions 100 mm and 150 mm apart from the needle electrodes of the needle electrode rod (1) so that the wire electrodes were located 20 mm above and apart from the film.

The ground electrode on which the film was placed was disposed so as to move horizontally (the direction indicated by the double-headed arrow in FIG. 1) under the needle electrodes and the wire electrodes.

The film was moved so that the film was completely outside the needle electrodes (first electrode). After a voltage of −10 kV was applied to the needle electrodes (first electrode), and a voltage of −15 kV was applied to the wire electrodes (second electrode), the vinylidene fluoride/tetrafluoroethylene copolymer resin film was passed at a rate of 96 cm/min under a corona discharge generated from the tips of the needle electrodes (first electrode) and the subsequent wire electrodes (second electrodes).

After the application of voltage, the charge on the film surface was removed using an grounded aluminum plate. The film was then removed from the SUS plate, and the surface state was observed.

The film was attached to the SUS plate by a corona discharge spreading concentrically from the tips of the needle electrodes. The farther away from the needle electrodes, the more insufficient the attachment of the film became; however, air left between the film and the SUS plate after the film was passed under the needle electrodes (first electrodes) was hardly observed. The resulting polarized film was transparent and had very few defects. Table 1 shows the evaluation data of the total light transmittance, total haze value, electromechanical coupling coefficient, and the number of spot defects per 150×300 mm square.

Example 2

A corona treatment was performed in the same manner as in Example 1, except that the electrodes (2) having a needle distance of 15 mm were used as the needle electrodes. As a result, air was observed between the individual needle electrodes. The resulting polarized film was transparent, but had more convex defects than Example 1. Table 1 shows the evaluation data of the total light transmittance, total haze value, electromechanical coupling coefficient, and the number of spot defects per 150×300 mm square.

Example 3

A corona treatment was performed in the same manner as in Example 1, except that the wire electrode (3) was used in place of the needle electrodes. Unlike the case using the needle electrodes, air left between the vinylidene fluoride/tetrafluoroethylene copolymer fluorine resin film and the ground electrode was observed in many portions. The resulting polarized film was transparent, but had more convex defects than Example 2. Table 1 shows the evaluation data of the total light transmittance, total haze value, electromechanical coupling coefficient, and the number of spot defects per 150×300 mm square.

Comparative Example 1

A corona treatment was performed in the same manner as in Example 1, except that the first electrode was not used, and only wire electrodes were used as the second electrode for polarization. Air left between the vinylidene fluoride/tetrafluoroethylene copolymer fluorine resin film and the ground electrode was observed in many portions. The resulting polarized film was transparent, but had many convex defects. Further, the number of convex defects was larger than Examples 1, 2, and 3. Table 1 shows the evaluation data of the total light transmittance, total haze value, electromechanical coupling coefficient, and the number of spot defects per 150×300 mm square.

TABLE 1

| | Total light transmittance | Total haze value | Electromechanical coupling coefficient | Number of spot defects per 150 × 300 mm square |
|---|---|---|---|---|
| Example 1 | 95% | 1.80% | 0.065 | 0 |
| Example 2 | 95% | 2.07% | 0.062 | 50 |
| Example 3 | 95% | 2.15% | 0.063 | 90 |
| Comparative Example 1 | 95% | 2.60% | 0.059 | 105 |

INDUSTRIAL APPLICABILITY

The polarized resin film of the present invention can be used as an optical film.

REFERENCE SIGNS LIST

1. Production apparatus
2. Ground electrode
3. First electrode
4. Second electrode
5. First high-voltage power supply
6. Second high-voltage power supply
7. Non-polarized resin film

The invention claimed is:

1. A method for producing a polarized resin film, comprising:
   step A of charging a non-polarized resin film directly placed on a ground electrode by a corona treatment using a first electrode while applying a voltage between the first electrode and the ground electrode, thereby attaching the non-polarized resin film to the ground electrode by static electricity; and
   step B of polarizing the non-polarized resin film attached to the ground electrode by a corona treatment using a second electrode while applying a voltage between the second electrode and the ground electrode.

2. The production method according to claim 1, wherein step A is carried out while the non-polarized resin film directly placed on the ground electrode is moved relative to the first electrode, and
   the first electrode comprises a plurality of needle electrodes arranged perpendicular to the moving direction.

3. The production method according to claim 1, wherein the non-polarized resin film is an odd-chain nylon film or a polyvinylidene fluoride-based resin.

4. The production method according to claim 1, wherein the non-polarized resin film is a polyvinylidene fluoride-based resin.

5. The production method according to claim 4, wherein the polyvinylidene fluoride-based resin is a vinylidene fluoride/tetrafluoroethylene copolymer resin film.

6. An apparatus for producing a polarized resin film, comprising a first electrode and a second electrode;
   wherein the first electrode is provided to face a ground electrode to be moved, and generates a corona discharge upon a voltage applied between the first electrode and the ground electrode, thereby charging a non-polarized resin film placed on the ground electrode so that the non-polarized resin film is attached to the ground electrode by static electricity; and
   the second electrode is provided downstream of the first electrode to face the ground electrode, and generates a corona discharge upon a voltage applied between the second electrode and the ground electrode, thereby polarizing the non-polarized resin film attached to the ground electrode.

7. The production apparatus according to claim 6, wherein the first electrode comprises a plurality of needle electrodes arranged at predetermined intervals perpendicular to the moving direction of the ground electrode.

8. The production apparatus according to claim 7, wherein the plurality of needle electrodes are arranged at intervals that are set so that a charged area of the non-polarized resin film that can be charged by a corona discharge overlaps at least part of a charged area of the non-polarized resin film charged by an adjacent needle electrode.

9. The production apparatus according to claim 6, wherein the second electrode comprises a wire electrode extending perpendicular to the moving direction.

10. The production method according to claim 2, wherein the non-polarized resin film is an odd-chain nylon film or a polyvinylidene fluoride-based resin.

11. The production method according to claim 2, wherein the non-polarized resin film is a polyvinylidene fluoride-based resin.

12. The production method according to claim 11, wherein the polyvinylidene fluoride-based resin is a vinylidene fluoride/tetrafluoroethylene copolymer resin film.

13. The production apparatus according to claim 7, wherein the second electrode comprises a wire electrode extending perpendicular to the moving direction.

14. The production apparatus according to claim 8, wherein the second electrode comprises a wire electrode extending perpendicular to the moving direction.

* * * * *